US009532554B2

(12) United States Patent
Taniguchi et al.

(10) Patent No.: US 9,532,554 B2
(45) Date of Patent: Jan. 3, 2017

(54) METHOD FOR INDUCING HEPATOCELLULAR VARIATION, AND PRODUCTION METHOD FOR CHIMERIC NON-HUMAN ANIMAL HAVING HUMANIZED LIVER

(71) Applicant: PUBLIC UNIVERSITY CORPORATION YOKOHAMA CITY UNIVERSITY, Yokohama-shi, Kanagawa (JP)

(72) Inventors: Hideki Taniguchi, Yokohama (JP); Yun-Wen Zheng, Yokohama (JP)

(73) Assignee: PUBLIC UNIVERSITY CORPORATION YOKOHAMA CITY UNIVERSITY, Yokohama-Shi, Kanawaga (JP)

( * ) Notice: Subject to any disclaimer, the term of this patent is extended or adjusted under 35 U.S.C. 154(b) by 0 days.

(21) Appl. No.: 14/348,196

(22) PCT Filed: Sep. 28, 2012

(86) PCT No.: PCT/JP2012/075019
§ 371 (c)(1),
(2) Date: Mar. 28, 2014

(87) PCT Pub. No.: WO2013/047720
PCT Pub. Date: Apr. 4, 2013

(65) Prior Publication Data
US 2014/0230080 A1 Aug. 14, 2014

(30) Foreign Application Priority Data

Sep. 30, 2011 (JP) ................................. 2011-215977

(51) Int. Cl.
*A01K 67/027* (2006.01)
*C12N 15/00* (2006.01)
*G01N 33/00* (2006.01)
*C12N 5/071* (2010.01)
*G01N 33/50* (2006.01)

(52) U.S. Cl.
CPC ........... *A01K 67/0271* (2013.01); *C12N 5/067* (2013.01); *G01N 33/5067* (2013.01); *G01N 33/5091* (2013.01); *A01K 2207/12* (2013.01); *A01K 2207/15* (2013.01); *A01K 2217/30* (2013.01); *A01K 2227/105* (2013.01); *A01K 2267/03* (2013.01); *C12N 2500/38* (2013.01); *C12N 2501/11* (2013.01); *C12N 2501/12* (2013.01); *C12N 2501/33* (2013.01); *C12N 2501/39* (2013.01); *C12N 2533/54* (2013.01); *G01N 2500/10* (2013.01)

(58) Field of Classification Search
CPC ........... A01K 67/0271; A01K 2207/12; A01K 2207/15; A01K 2227/105; G01N 33/5067

USPC ................................................ 800/3, 18, 21
See application file for complete search history.

(56) References Cited

U.S. PATENT DOCUMENTS

| 2007/0148141 A1 | 6/2007 | Johnston et al. |
| 2008/0311094 A1 | 12/2008 | Sokal et al. |
| 2011/0104126 A1* | 5/2011 | Taniguchi et al. |

FOREIGN PATENT DOCUMENTS

| EP | 2 295 537 A1 | 3/2011 |
| JP | 2009-520474 A | 5/2009 |
| WO | WO 01/32009 A1 | 5/2001 |
| WO | WO 01/67854 A1 | 9/2001 |
| WO | WO 2004/027029 A2 | 4/2004 |
| WO | WO 2009/139419 A1 | 11/2009 |

OTHER PUBLICATIONS

Wu et al., 2012, Aging Research reviews, vol. 11, p. 32-40.*
Steinert et al., 2007, Arthritis Research & therapy, vol. 9, No. 3, 213, p. 1-15.*
Li et al., 2009, Transplant Immunology, vol. 21, p. 70-74.*
Sprangers et al., 2008, Kidney International, vol. 74, p. 14-21.*
Extended European Search Report issued Feb. 10, 2015, in European Patent Application No. 12837488.1.
Liu et al., "In Vivo Liver Regeneration Potential of Human Induced Pluripotent Stem Cells from Diverse Origins," Science Translational Medicine, May 2011 Compilation, vol. 3, Issues 81-84, pp. 85-94.
Su et al., "Xeno-repopulation of $Fah^{-1}$-$Nod/Scid$ mice livers by human hepatocytes," Science China Life Sciences (Mar. 2011), vol. 54, No. 3, pp. 227-234.
Suemizu et al., "Establishment of a humanized model of liver using NOD/$Shi$-$scid$ IL2Rg$^{null}$ mice," Biochemical and Biophysical Research Communications (2008), vol. 377, pp. 248-252.
Wang et al., "Albumin-expressing hepatocyte-like cells develop in the livers of immune deficient mice that recieved transplants of highly purified human hematopoietic stem cells," Blood (2003), vol. 101, No. 10, pp. 4201-4208.

(Continued)

Primary Examiner — Shin Lin Chen
(74) Attorney, Agent, or Firm — Birch, Stewart, Kolasch & Birch, LLP

(57) ABSTRACT

The present invention provides (1) a method for producing a non-human animal having a humanized liver, comprising transplanting human hepatic stem cells and/or hepatic progenitor cells and/or immature hepatocytes to a liver-damaged non-human animal to induce the differentiation of the cells into hepatocytes, (2) a non-human animal having a humanized liver, produced by the method, (3) a method for examining the pharmacokinetics and/or hepatotoxicity of a test substance, comprising using the animal, (4) a method for producing human hepatocytes, comprising transplanting human hepatic stem cells and/or hepatic progenitor cells and/or immature hepatocytes to a liver-damaged non-human animal to induce the differentiation of the cells into hepatocytes, and (5) a method for examining the pharmacokinetics and/or hepatotoxicity of a test substance, comprising using human hepatocytes produced by the method.

8 Claims, 12 Drawing Sheets

(56) References Cited

OTHER PUBLICATIONS

Washburn et al., "A Humanized Mouse Mode to Study Heptatitis C Virus Infection, Immune Response, and Liver Disease," Gastroenterology (2011), vol. 140, pp. 1334-1344.
International Preliminary Report on Patentability issued Jul. 24, 2013, in PCT International Application No. PCT/JP2012/075019, with English translation.
Banas et al., " IFATS Collection: In Vivo Therapeutic Potential of Human Adipose Tissue Mesenchymal Stem Cells After Transplantation into Mice with Liver Injury", pp. 2705-2712, Stem Cells, Jun. 5, 2008.
International Search Report for PCT/JP2012/075019 dated Jan. 8, 2013.
Ishii et al., "Transplantation of Embryonic Stem Cell-Derived Endodermal Cells into Mice with Induced Lethal Liver Damage", vol. 25, pp. 3252-3260, Stem Cells, 2007.
Machimoto et al., "Improvement of the Survival Rate by Fetal Liver Cell Transplantation in a Mice Lethal Liver Failure Model", vol. 84, No. 10, pp. 1233-1239, Transplantation, Nov. 27, 2007.
Saito et al., "Diphtheria toxin receptor-mediated conditional and targeted cell ablation in transgenic mice", Nature Biotechnology, vol. 19, pp. 746-750, Aug. 2001.
Saito et al., "Generation of mouse models of human disease using a diphtheria toxin receptor-mediated conditional cell knockout method", Protein, Nucleic Acid and Enzyme,vol. 54, No. 5, pp. 614-620, 2009.
Schmelzer et al., "Human hepatic stem cells from fetal and postnatal donors", vol. 24, No. 8, pp. 1973-1987, Journal of Experimental Medicine, Aug. 6, 2007.
Suemizu et al., "Establishment of a humanized model of liver using NOD/Shi-scid IL2Rgnull mice", Biochemical and Biophysical Research Communications, vol. 377, pp. 248-252, 2008.
Zagoura et al., "Therapeutic potential of a distinct population of human amniotic fluid mesenchymal stem cells and their secreted molecules in mice with acute hepatic failure", vol. 61, pp. 894-906, Gut 2012.

\* cited by examiner

Tx: 8wk
FLC=human fetal liver cells;
HSC=human hepatic stem cells;
C3=BMI1-HSC Clone3

```
                               SEQUENCE LISTING

<160> NUMBER OF SEQ ID NOS: 6

<210> SEQ ID NO 1
<211> LENGTH: 24
<212> TYPE: DNA
<213> ORGANISM: Artificial Sequence
<220> FEATURE:
<223> OTHER INFORMATION: Primer

<400> SEQUENCE: 1
gcacaatgaa gatcaagatc attg                                             24

<210> SEQ ID NO 2
<211> LENGTH: 21
<212> TYPE: DNA
<213> ORGANISM: Artificial Sequence
<220> FEATURE:
<223> OTHER INFORMATION: Primer

<400> SEQUENCE: 2
taaagccatg ccaatctcat c                                                21

<210> SEQ ID NO 3
<211> LENGTH: 24
<212> TYPE: DNA
<213> ORGANISM: Artificial Sequence
<220> FEATURE:
<223> OTHER INFORMATION: Primer

<400> SEQUENCE: 3
aagatcaaga tcattgctcc tcct                                             24

<210> SEQ ID NO 4
<211> LENGTH: 22
<212> TYPE: DNA
<213> ORGANISM: Artificial Sequence
<220> FEATURE:
<223> OTHER INFORMATION: Primer

<400> SEQUENCE: 4
gccatgccaa tgttgtctct ta                                               22

<210> SEQ ID NO 5
<211> LENGTH: 21
<212> TYPE: DNA
<213> ORGANISM: Artificial Sequence
<220> FEATURE:
<223> OTHER INFORMATION: Primer

<400> SEQUENCE: 5
gcaccacacc ttctacaatg a                                                21

<210> SEQ ID NO 6
<211> LENGTH: 20
<212> TYPE: DNA
<213> ORGANISM: Artificial Sequence
<220> FEATURE:
<223> OTHER INFORMATION: Primer
```

```
<400> SEQUENCE: 6
gctggggtgt tgaaggtctc                                              20
```

METHOD FOR INDUCING HEPATOCELLULAR VARIATION, AND PRODUCTION METHOD FOR CHIMERIC NON-HUMAN ANIMAL HAVING HUMANIZED LIVER

TECHNICAL FIELD

The present invention relates to a method for inducing differentiation into hepatocytes and a method for producing a chimeric non-human animal having a humanized liver.

BACKGROUND ART

Previous reports describe induction of the differentiation of immature hepatocytes and the functional maintenance of the differentiated hepatocytes using in vitro cell culture methods such as 2D culture, 3D culture, and coculture. Such hepatocytes differentiated in vitro, however, are difficult to maintain functionally, as compared with in vivo adult hepatocytes. On the other hand, human adult hepatocytes are poorly proliferative and scarcely available and are therefore difficult to supply in large quantities to the pharmaceutical industry.

Mercer, Mukaidani, et al. have reported that when cryopreserved human hepatocytes were transplanted into immunodeficient mice with liver damage (uPA-Tg/scid), approximately 50 to 70% of the liver was replaced with human hepatocytes in vivo (Non Patent Literature 1: Nat Med 7: 927-933, 2001; and Patent Literature 1: WO2003/080821). Nonetheless, the production of chimeric mice having human-derived hepatocytes from the uPA-Tg/scid mice is still insufficient means for large-scale proliferation of human hepatocytes, though the chimeric mice can be useful in themselves. In addition, the human hepatocyte-transplanted chimeric mice are incapable of long-term survival (shorter than 50 days) and mouse hepatocytes proliferate in the course of growth, so their applicability to systems for in vivo evaluation of toxicity against or drug efficacy for human hepatocytes is limited.

In addition, Su et al. have reported that in a transplantation of human hepatocytes into a $Fah^{-/-}NOD/scid$ model, the replacement with human hepatocytes was approximately 33.6% at maximum (Non Patent Literature 2: Sci China Life Sci 54: 227-234, 2011). Bissing et al. have reported that in a transplantation using $Fah^{-/-}/Rag2^{-/-}/Il2rg^{-/-}$ triple KO mice, the replacement with human hepatocytes was approximately 20% at maximum (Non Patent Literature 3: Proc Natl Acad Sci 104(51): 20507-20511, 2007). Immunodeficient TRECK mice, which are transgenic mice developed by Saito et al., express a diphtheria toxin receptor human HB-EGF in particular cells and permit specific ablation of target cells through the administration of diphtheria toxin at any stage of time course (Non Patent Literature 4: Nat Biotechnol.; 19(8): 746-50, 2001). Also, Matsumoto et al. have reported that a transplantation of mouse fetal hepatocytes into TRECK-based hepatitis model mice (Alb-TRECK) improved the rate of their survival (Non Patent Literature 5: Transplantation; 84(10): 1233-9, 2007). Ishii et al. have reported that a transplantation of hepatocytes derived from mouse embryonic stem cells into immunodeficient Alb-TRECK mice improved the rate of 35-day survival (Non Patent Literature 6: Stem Cells. 25(12): 3252-60, 2007). Matsuoka et al. have reported that human albumin was detected in blood when human adult hepatocytes were transplanted into immunodeficient Alb-TRECK mice (Non Patent Literature 7: "Method for producing human liver-chimerized Tg mice" Hiromichi Yonekawa, Kunie Matsuoka, The Tokyo Metropolitan Institute of Medical Science/disease model development center, the 7th research exchange forum, 2008 Feb. 27, Tokyo, Japan).

CITATION LIST

Non Patent Literature

Non Patent Literature 1: Nat Med 7: 927-933, 2001
Non Patent Literature 2: Sci China Life Sci 54: 227-234, 2011
Non Patent Literature 3: Proc Natl Acad Sci 104(51): 20507-20511, 2007
Non Patent Literature 4: Nat Biotechnol; 19(8): 746-50, 2001
Non Patent Literature 5: Transplantation; 84(10): 1233-9, 2007
Non Patent Literature 6: Stem Cells. 25(12): 3252-60, 2007
Non Patent Literature 7: "Method for producing human liver-chimerized Tg mice" Hiromichi Yonekawa, Kunie Matsuoka, The Tokyo Metropolitan Institute of Medical Science/disease model development center, the 7th research exchange forum, 2008 Feb. 27, Tokyo, Japan

Patent Literature

Patent Literature 1: International Publication No. WO2003/080821

SUMMARY OF INVENTION

Technical Problem

Heretofore, there have been the following problems:
1. Methods of inducing the differentiation using ex vivo cell culture methods have not yet been established.
2. Human adult hepatocytes are not only poorly proliferative but also scarcely available.
3. Chimeric mice prepared by use of adult hepatocytes are unsuitable for industrial application due to their low transplantation efficiency and high production cost.
4. No chimeric mice have been reported in which transplanted human cells proliferate fast to exhibit high chimerism efficiency after the transplantation.
5. Humans and laboratory animals largely differ in the capacity to metabolize chemicals. Accordingly, possible effects on humans are difficult to predict accurately from the results obtained using laboratory animals.

Heretofore, the transplantation of human hepatocytes has been practiced in various types of mice (uPA-Tg/scid, $Fah^{-/-}$ NOD/scid, $Fah^{-/-}/Rag2^{-/-}/Il2rg^{-/-}$ triple KO, etc.). Nonetheless, engraftment efficiency still remains to be improved.

An object of the present invention is to solve the problems of the conventional techniques and provide a method for inducing differentiation into hepatocytes and a method for producing a chimeric non-human animal having a humanized liver.

Solution to Problem

The present inventors performed transplantation using severely immunodeficient transgenic mice (Alb-TRECK/scid mice) which were forced to express a diphtheria toxin receptor only in hepatocytes. Use of the Alb-TRECK/scid mice can cause a hepatocyte-specific disorder and is expected to enhance the chimerism efficiency of human hepatocytes. The conventional Alb-TRECK/scid mice are generated by crossing liver damage transgenic mice (Alb-TRECK) with severely immunodeficient mice (SCID). By contrast, the present inventors newly produced Alb-TRECK mice on an SCID background (Alb-TRECK/scid) and thereby achieved drastic reduction in mouse production cost.

Conventional transplantation models using adult hepatocytes have poor chimerism efficiency and also require high production cost. Thus, the present inventors used human fetal liver stem/progenitor cells and immature human hepatocytes as donor cells. These cells are capable of high proliferation and feature stable supply, as compared with adult hepatocytes. In vitro methods, however, had not yet been established for induction of the differentiation of human fetal liver stem/progenitor cells or immature human hepatocytes and for the functional maintenance of the differentiated cells.

The present inventors made the following improvements by using Alb-TRECK/scid mice as a recipient and human fetal liver stem/progenitor cells or immature hepatocytes as a donor:

1. The chimerism efficiency of human-derived cells in the liver was enhanced.
2. The differentiation of human fetal liver stem/progenitor cells or immature hepatocytes was induced by in vivo transplantation.

Also, similar or higher effects were confirmed in uPA-NOG mice with spontaneous liver damage.

The present invention is summarized as follows:

(1) A method for producing a non-human animal having a humanized liver, comprising transplanting human hepatic stem cells and/or hepatic progenitor cells and/or immature hepatocytes to a liver-damaged immunodeficient non-human animal to induce the differentiation of the cells into hepatocytes.

(2) The method according to (1), wherein the liver damage is hepatocyte-specific.

(3) The method according to (1) or (2), wherein the liver-damaged non-human animal is a non-human animal with hepatitis caused by the administration of diphtheria toxin to an immunodeficient non-human animal that expresses a diphtheria toxin receptor human HB-EGF in hepatocytes.

(4) The method according to any of (1) to (3), wherein the human hepatic stem cells and/or hepatic progenitor cells and/or immature hepatocytes are CDCP1-positive/CD90-positive/CD66-negative cells.

(5) The method according to (4), wherein the human hepatic stem cells and/or hepatic progenitor cells and/or immature hepatocytes are CDCP1-positive/CD90-positive/CD66-negative/CD13-positive cells.

(6) A non-human animal having a humanized liver, produced by a method according to any of (1) to (5).

(7) A method for examining the pharmacokinetics and/or hepatotoxicity of a test substance, comprising using a non-human animal according to (6).

(8) A method for producing human hepatocytes, comprising transplanting human hepatic stem cells and/or hepatic progenitor cells and/or immature hepatocytes to a liver-damaged non-human animal to induce the differentiation of the cells into hepatocytes.

(9) A method for examining the pharmacokinetics and/or hepatotoxicity of a test substance, comprising using human hepatocytes produced by a method according to (8).

Advantageous Effects of Invention

1. Alb-TRECK/scid mice that can be used as a recipient are easy to handle in breeding and propagation. The present invention is thus adaptable to large-scale production as a preliminary step toward industrial application and also has considerable cost benefits. Moreover, the present invention can be readily carried out because methods for causing liver damage have been established.

2. Human fetal liver stem/progenitor cells and immature hepatocytes are capable of high proliferation and can also be engrafted in vivo with high probability, as compared with adult hepatocytes. Use of these properties enables large-scale in vivo production of human hepatocytes in animals.

3. Chimeric mouse models based on Alb-TRECK/scid mice have a chimera rate of human hepatocytes as high as 84.5% and a survival time exceeding 100 days. The expression of liver-specific functional genes in the models is comparable to that in human fetal liver tissues.

The present specification encompasses the contents described in the specification and/or drawings of Japanese Patent Application No. 2011-215977 on which the priority of the present application is based.

DESCRIPTION OF EMBODIMENTS

Figure 1:
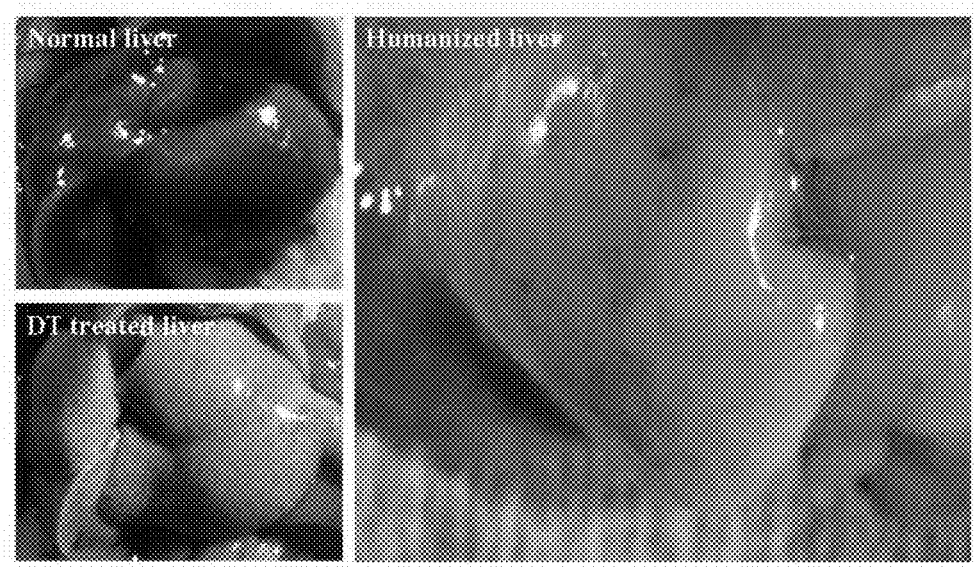
FIG. 1 shows the difference of an Alb-TRECK/SCID mouse liver before and after transplantation. The state of the Alb-TRECK/SCID mouse liver was compared between before and after transplantation. The upper left image shows the normal liver before DT treatment. The lower left image shows the liver 48 hours after DT administration. As is evident from its appearance, the liver that received DT turned white due to liver damage. The liver that received DT, however, changed better in color and was restoring its normal state 5 weeks after transplantation of hepatic stem cells (right image). The transplantation of hepatic stem cells to the severely injured liver reconstituted tissues and mitigated the liver damage.

Hereinafter, the present invention will be described in more detail.

The present invention provides a method for producing a non-human animal having a humanized liver, comprising transplanting human hepatic stem cells and/or hepatic progenitor cells and/or immature hepatocytes to a liver-damaged immunodeficient non-human animal to induce the differentiation of the cells into hepatocytes.

The liver-damaged immunodeficient non-human animal preferably has hepatocyte-specific liver damage. The liver-damaged immunodeficient non-human animal can be produced by the liver damage induction treatment of an immunodeficient non-human animal. Examples of the immunodeficient non-human animal may include animals rendered immunodeficient by the deficiency of B cells, T cells, or NK cells (e.g., non-human animals deficient in genes such as Rag1, Rag2, Jak3, or/and Foxn1). Specific examples may include model animals such as NOD/SCID/Jak3$^{-/-}$, Nude/Jak3$^{-/-}$, NOG (NOD/Shi-SCID/IL2R$\gamma^{-/-}$) NOD/RAG2$^{-/-}$/IL2R$\gamma^{-/-}$, Nude/RAG2$^{-/-}$, BALB/cA-RAG2$^{-/-}$/IL2R$\gamma^{-/-}$, NOD–. scid, NOD, SCID, and X-SCID (IL2R$\gamma^{-/-}$). Examples of the liver damage induction treatment may include: genetic modification which results in Alb-TRECK Tg animals, Alb-uPA Tg animals, Alb-herpes virus thymidine kinase (HSV-TK) Tg animals, Fah–/– animals, etc.; administration of drugs such as retrorsine, 2AAF, DEN, or CC14; immune response caused by the addition of an anti-Fas antibody, etc.; and physical disorder caused by hepatectomy, irradiation, etc. When the liver-damaged immunodeficient non-human animal is a genetically modified animal, it is preferable to use an animal in which the modified gene is a homozygote.

Specific examples of the liver-damaged immunodeficient non-human animal may include: a non-human animal with hepatitis caused by the administration of diphtheria toxin to an immunodeficient non-human animal that expresses a diphtheria toxin receptor human HB-EGF in hepatocytes; and a non-human animal prepared by the administration of drugs to a normal non-human animal and subsequent resection of the liver.

Examples of the immunodeficient non-human animal that expresses a diphtheria toxin receptor human HB-EGF (heparin-binding EGF-like growth factor) in hepatocytes may include, but are not limited to, transgenic mice (SCID-Alb-TRECK-Tg mice) produced by the microinjection of a recombinant DNA having a human-derived diphtheria toxin (DT) receptor gene linked to a mouse albumin (ALB) promoter to the pronuclei of fertilized eggs of a severe combined immunodeficiency mouse (SCID mouse) ("Method for producing human liver-chimerized Tg mice" Hiromichi Yonekawa, Kunie Matsuoka, The Tokyo Metropolitan Institute of Medical Science/disease model development center, the 7th research exchange forum, 2008 Feb. 27, Tokyo, Japan), and progeny thereof. The SCID-Alb-TRECK-Tg mice are preferably homozygous for the DT receptor allele that is driven by the ALB promoter. Such homozygosity can be secured by back crossing. Examples of the non-human animal may include mammals such as mice, rats, hamsters, guinea pigs, rabbits, cattle, pigs, sheep, goats, dogs, monkeys, chimpanzees, and gorillas.

Hepatitis is caused by the administration of diphtheria toxin to the immunodeficient non-human animal (recipient) that expresses a diphtheria toxin receptor human HB-EGF in hepatocytes. Then, the human hepatic stem cells and/or hepatic progenitor cells and/or immature hepatocytes are transplanted to the animal. In the case of using a SCID-Alb-TRECK-Tg mouse, for example, diphtheria toxin can be administered thereto at a dose of 1.0 to 1.5 µg/kg to thereby develop hepatitis.

Preferably, Anti-asialo GM1 is administered for NK cell depletion to the recipient that has received diphtheria toxin.

The development of hepatitis can be confirmed by sampling blood from the recipient and determining the activity of transaminase (GOT) and alanine transaminase (GPT) in serum components. The recipient is regarded as having hepatitis if the values of transaminase (GOT) activity and alanine transaminase (GPT) activity are 5000 or higher and 10000 or higher, respectively.

The human hepatic stem cells and/or hepatic progenitor cells and/or immature hepatocytes (donor cells) to be transplanted to the recipient are preferably cells that express phenotypic markers, such as E-cadherin, EpCam, Dlk, NCAM, ICAM-1, CD14, CD29, CD34, CD44, CD49f, CD133, CDCP1, CD90, and/or CD13, which are expressed in human hepatic stem cells and/or hepatic progenitor cells and/or immature hepatocytes. One example that can be given is cells that have CDCP1-positive/CD90-positive/CD66-negative phenotype. The donor cells that can be used in the present invention are CDCP1-positive/CD90-positive/CD66-negative cells as separated by FACS from, for example, human primary fetal hepatocytes supplied by Dainippon Pharmaceutical Co., Ltd. (Cat No. CS-ABI-3716) or cultured or subcultured cells thereof. Preparation methods for these cells are described in WO2009/139419. More preferably, the donor cells are CD13-positive. CD13 is a marker for liver stem/progenitor cells. Alternatively, hepatic stem cells and/or hepatic progenitor cells and/or immature hepatocytes that have been induced to differentiate from iPS cells, ES cells, or the like may be used. Methods for inducing the differentiation of iPS cells, ES cells, or the like into these hepatic stem cells and/or hepatic progenitor cells and/or immature hepatocytes are described in Cell Res. 2009; 19(11): 1233-42 and Mol Ther. 2011; 19(2): 400-7, for example.

The donor cells are preferably transplanted to the spleen, portal vein, mesenterium, or renal capsule of the recipient, beneath the skin of the recipient, or the like.

After the donor cell transplantation, the engraftment of the donor cells in the recipient can be confirmed by, for example, H & E staining and immunostaining (see Examples to be described later).

Induction of the differentiation of the transplanted human hepatic stem cells and/or hepatic progenitor cells and/or immature hepatocytes (donor cells) into hepatocytes can be confirmed by, for example, the immunostaining of human albumin and human CK19 (see Examples to be described later). The recipient can be regarded as having a humanized liver or its liver can be regarded as having been humanized, if it is confirmed that the human hepatic stem cells and/or hepatic progenitor cells and/or immature hepatocytes (donor cells) transplanted to the recipient have been successfully induced to differentiate into hepatocytes and are capable of maintaining human liver functions for a given duration. For example, when an SCID-Alb-TRECK-Tg mouse affected by hepatitis is transplanted with $1\times10^6$ human hepatic stem cells and/or hepatic progenitor cells and/or immature hepatocytes, induction for differentiation into hepatocytes is observed approximately 30 to 60 days after the transplantation.

The present invention also provides a non-human animal having a humanized liver, produced by the method described above.

The non-human animal having a humanized liver according to the present invention is capable of expressing human-derived drug-metabolizing enzymes (e.g., CYP3A4, CYP2C9, CYP2C19, 2D6, and 1A2). The humanized liver in this animal is therefore considered to metabolize drugs in a similar manner to the human liver. Thus, the examination of the pharmacokinetics and/or hepatotoxicity of a test substance using this animal is useful in research for drug discovery. The present invention provides a method for examining the pharmacokinetics and/or hepatotoxicity of a test substance, comprising using a non-human animal having a humanized liver, produced by transplanting human hepatic stem cells and/or hepatic progenitor cells and/or immature hepatocytes to a liver-damaged non-human animal to induce the differentiation of the cells into hepatocytes.

In an alternative aspect of the present invention, human hepatocytes can be produced by transplanting human hepatic stem cells and/or hepatic progenitor cells and/or immature hepatocytes to a liver-damaged non-human animal to induce the differentiation of the cells into hepatocytes. Specifically, the present invention provides a method for producing human hepatocytes, comprising transplanting human hepatic stem cells and/or hepatic progenitor cells and/or immature hepatocytes to a liver-damaged non-human animal to induce the differentiation of the cells into hepatocytes. The human hepatocytes produced by this method are capable of expressing human-derived drug-metabolizing enzymes (e.g., CYP3A4, CYP2C9, CYP2C19, 2D6, and 1A2) and therefore considered to metabolize drugs in a similar manner to naturally occurring human hepatocytes. Thus, the examination of the pharmacokinetics and/or hepatotoxicity of a test substance using these cells is useful in research for drug discovery. The present invention provides a method for examining the pharmacokinetics and/or hepatotoxicity of a test substance, comprising using human hepatocytes produced by transplanting human hepatic stem cells and/or hepatic progenitor cells and/or immature hepatocytes to a liver-damaged non-human animal to induce the differentiation of the cells into hepatocytes.

The test substance may be any substance. Examples thereof may include proteins, peptides, vitamins, hormones, polysaccharides, oligosaccharides, monosaccharides, low-molecular-weight compounds, nucleic acids (DNAs, RNAs, oligonucleotides, mononucleotides, etc.), lipids, natural compounds other than those described above, synthetic compounds, plant extracts, and fractions of plant extracts, and mixtures thereof.

The test substance can be examined for its pharmacokinetics and/or hepatotoxicity by a routine method.

To examine the test substance for its pharmacokinetics, it may, for example, be administered to a non-human animal or added to human hepatocytes. Then, its metabolites or excrement, plasma, liver tissues, or the like are recovered and assayed by a suitable method such as mass spectrometry or HPLC analysis.

To examine the test substance for its hepatotoxicity, it may, for example, be administered to a non-human animal or added to human hepatocytes. Then, the hepatocytes are observed for its state (e.g., necrosis). Alternatively, human albumin, GOT, GPT, LDH, and the like in the blood of the non-human animal may be assayed.

EXAMPLES

Hereinafter, the present invention will be described specifically with reference to Examples. However, the present invention is not intended to be limited by these Examples. In Examples below, Alb-TRECK/SCID mice are referred to as TRECK/SCID mice.

Example 1

1. Materials and Methods

Source of Human Hepatocyte

Human fetal liver cells used in this research were separated by ACBRI (Applied Cell Biology Research Institute, a registered Washington non-profit research institution, USA) by consent of the provider and donated by Cell Systems Corp. (USA) without charge (Cat No. CS-ABI-3716). In Japan, human primary fetal hepatocytes were supplied by Dainippon Pharmaceutical Co., Ltd. (Cat No. CS-ABI-3716) and used in this research. The cells were negative in the tests of infections (HIV, HBV, and HCV) and the tests of microbes (fungi, bacteria, and mycoplasma). This research was deliberated and approved by the ethics committee of Yokohama City University.

Cell Culture and Subculture

An already established and reported low-density culture system of fetal liver cells capable of forming colonies (Zheng Y W, Taniguchi H, et al., Transplant Proc 2000; 32: 2372-2373; and Suzuki A, Zheng Y W, et al., Hepatology 2000; 32: 1230-1239) was modified as follows:

A DMEM/nutrient mixture F-12 Ham medium (DMEM/F12 1:1 mixture, SIGMA) supplemented with 10% fetal bovine serum (FBS), human γ-insulin (1.0 µg/ml, Wako, Japan), nicotinamide (10 mM, SIGMA), dexamethasone ($1 \times 10^{-7}$ M, SIGMA), and L-glutamine (2 mM, GIBCO BRL) was added to a collagen IV-coated dish (Becton Dickinson Labware). Primary fetal liver cells or cells fractionated by flow cytometry were seeded into the resulting medium and cultured over a period of approximately 2 to 3 weeks or longer. The medium was completely replaced with a fresh one every five days. Growth factors such as human recombinant HGF (50 ng/ml, SIGMA) and epithelial growth factor (EGF) (10 ng/ml, SIGMA) were added to the cells 24 hours after the seeding.

When becoming 90% confluent in the culture dish, the cells were subcultured by the following procedures: after removal of the culture medium, the cells were treated with 0.05% trypsin-EDTA (GIBCO) at room temperature for 5 minutes and detached from the culture dish by gentle tapping. The floating cells were washed with a culture medium containing 10% FBS and then reseeded into a culture medium. As a result of trypan blue staining, the survival rate of the dissociated cells did not fall below 90%. The seeding density of the cells was selected according to the experimental design from among single cell culture (approach of culturing one flow cytometry-sorted cell per well of a 96-well plate), low-density cell culture of 100 to 500 cells/cm$^2$, and high-density cell culture of $1 \times 10^3$ cells/cm$^2$.

Cell Profiling and Sorting by Flow Cytometry

Floating cells were incubated on ice for 30 minutes under the optimum concentration of a fluorescently labeled monoclonal antibody (mAb), while shielded from light. PBS supplemented with 2% FBS was used as a washing solution and an antibody-diluting solution. When a biotin-labeled primary antibody was used, secondary reaction was performed with a streptavidin-labeled fluorescent antibody. All fluorescently labeled monoclonal antibodies were purchased from Becton, Dickinson and Company: fluorescein isothiocyanate (FITC)-conjugated anti-human CD66 (hCD66FITC), allophycocyanin (APC)-conjugated hCD90, and phycoerythrin (PE)-conjugated hCD318. Sorting was performed using a high-speed cell sorter MoFlo (DakoCytomation). *CD318 is sometimes referred to as CDCP1.

Cytochemical and Immunocytochemical Assays

For multiple immunocytochemical staining, cells were fixed in cold ethanol for 30 minutes and blocked with 10% normal goat serum (NGS) for 60 minutes. Then, each primary antibody was diluted with PBS supplemented with 1% NGS, and reacted overnight with the cells at 4° C. in a moist chamber. Each secondary antibody was diluted with PBS containing 10% glycerol and reacted with the cells at room temperature for 60 minutes in a moist chamber. The cell nuclei were stained with DAPI. The cells were mounted in an FA mounting fluid. (Images were obtained under Zeiss AxioImager microscope.)

The primary antibodies used in the immunocytochemical assay were mouse anti-human albumin mAb (SIGMA), mouse anti-human CK19 mAb (Progen), guinea pig anti-CK8/18 pAb (Progen), and mouse anti-human Nuclei mAb (Millipore). The secondary antibodies used were Alexa 488-labeled goat anti-guinea pig IgG, Alexa 555-labeled goat anti-mouse IgG$_{2a}$, and Alexa 647-conjugated goat anti-mouse IgG$_1$ (Invitrogen, Molecular Probes).

Real-Time PCR

Cell- or cell colony-derived total RNA was extracted using Isogen reagent (Nippon Gene, Toyama, Japan). Before reverse transcription (RT), 150 ng of random primers and 1 µl of 10 mM dNTP mix were added to the total RNA solution. The reaction mixture was heated at 65° C. for 5 minutes and incubated on ice for 1 minute. Then, 1× first-strand buffer, 0.5 mM dNTP mix, 5 mM DTT, and 200 units of Super Script III (Invitrogen) were added, and the mixture was incubated at 25° C. for 5 minutes, 50° C. for 45 minutes, and 70° C. for 15 minutes to synthesize cDNA from the total RNA.

TaqMan probes and primers for albumin (Hs00609411_m1), AFP (Hs01040607_m1), CYP3A4 (Hs01546612_m1), CYP2C9 (Hs00426397_m1), CYP2C19 (Hs00426380_m1), and hACTB (4326315E) were purchased as TaqMan Gene Expression Assays (Applied Biosystems).

Production and Analysis of Chimeric Mouse

Mice used as a recipient in this research were TRECK/SCID mice (provided by The Tokyo Metropolitan Institute of Medical Science) generated by crossing target cell-knockout mice (toxin receptor mediated cell knockout mice: TRECK mice) with severely immunodeficient mice (SCID mice). In order to target mouse liver parenchymal cells, the recipient underwent transgenesis using a recombinant DNA having a human-derived diphtheria toxin receptor gene linked to a mouse ALB promoter. This allows only a human receptor-expressing organ to be specifically killed by the administration of diphtheria toxin. These mice kept a stable state by back crossing for three generations in order to render their genetic backgrounds uniform. Four- to 8-week-old TRECK/SCID mice were used in cell transplantation. Liver damage was caused by the administration of 1.5 ug/kg diphtheria toxin (DT) 48 hours before transplantation. Mouse NK cells were depleted by the administration of 100 ul of 1 mg/ml Anti-asialo GM1 (Wako, Japan). Blood was sampled from the tail vein of each mouse 48 hours after the DT administration and centrifuged at 4000 rpm at 4° C. for 20 minutes to obtain serum components. The activity of transaminase (GOT) and alanine transaminase (GPT) in the obtained serum components was determined using FUJIFILM DRY-CHEM kit. The spleen of each TRECK/SCID mouse with liver damage caused by the DT treatment was transplanted with $1 \times 10^6$ fetal hepatic stem cells (HSCs) or fetal liver cells (FLCs). Six weeks after the transplantation, the mouse livers were sampled and subjected to immunostaining, H & E staining, gene analysis, and ELISA. For the ELISA analysis, blood was sampled from the tail veins of the chimeric mice 4 weeks or longer after the transplantation, and serum components were separated and used as samples. The amount of human albumin secreted into the serum was measured using a human albumin ELISA kit (Bethyl Laboratories).

2. Experimental Results

Hepatic stem cells isolated from fetal liver cells (FLCs) were examined for in vivo capacity to be induced to differentiate and for functionality. The present inventors transplanted CDCP1-positive/CD90-positive/CD66-negative hepatic stem cells (HSCs) into TRECK/SCID mice that had their livers damaged by DT administration. Mouse livers reconstituted by the in vivo engrafted hepatic stem cells were sampled 40 days after the transplantation and analyzed histologically.

Difference of TRECK/SCID Mouse Liver Before and after Transplantation (FIG. 1)

The state of the TRECK/SCID mouse liver was compared by examination before and after transplantation. The upper left image shows the normal liver before DT treatment. The lower left image shows the liver 48 hours after DT administration. As is evident from its appearance, the liver that received DT turned white due to liver damage. The liver that received DT, however, changed better in color and was restoring its normal state 5 weeks after transplantation of hepatic stem cells (right image). The transplantation of hepatic stem cells to the severely injured liver reconstituted tissues and mitigated the liver damage.

Figure 2:
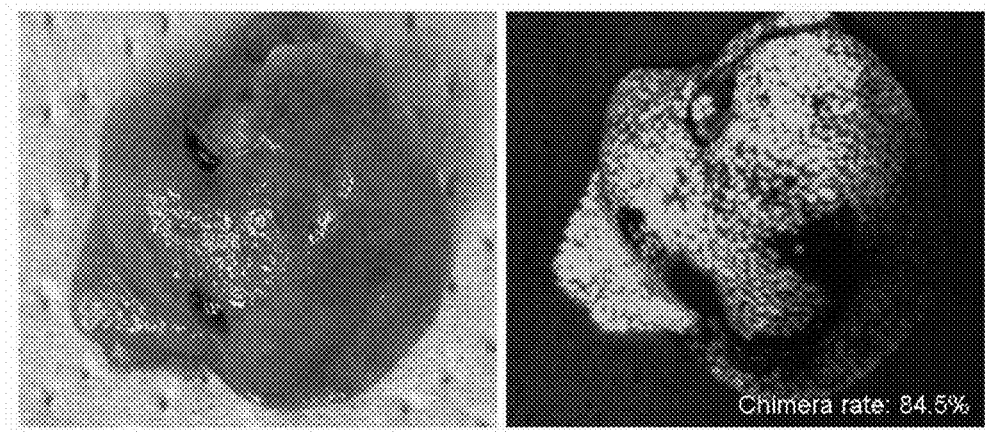
FIG. 2 shows the chimera rate of a humanized liver in a chimeric mouse. GFP-expressing hepatic stem cells were used in transplantation in order to visualize the engrafted state of transplanted hepatic stem cells more precisely. Twenty days after the transplantation, more than half of cells in the liver tissues were derived from the GFP-positive hepatic stem cells. The chimerism efficiency reached as high as 84.5%. Average chimera rate: 65.6±17.5% (n=3).

Chimera Rate of Humanized Liver in Chimeric Mouse (FIG. 2)

GFP-expressing hepatic stem cells were used in transplantation in order to more precisely visualize the engrafted state of transplanted hepatic stem cells more precisely. Twenty days after the transplantation, more than half of cells in the liver tissues were derived from the GFP-positive hepatic stem cells. The chimerism efficiency reached as high as 84.5%. Average chimera rate: 65.6±17.5% (n=3).

Figure 3:
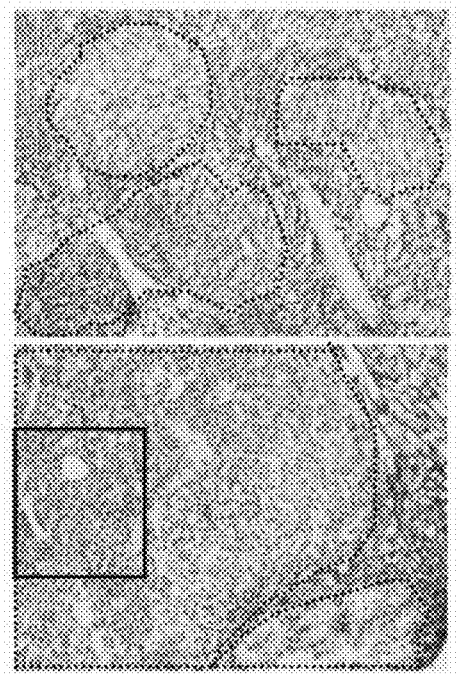
FIG. 3 shows the histological analysis of a humanized liver in a chimeric mouse (H & E staining and immunostaining). The produced human-derived chimeric liver was analyzed histologically. As a result of H & E staining, human-derived hepatic stem cells were observed (surrounded by dotted lines).
Figure 3:
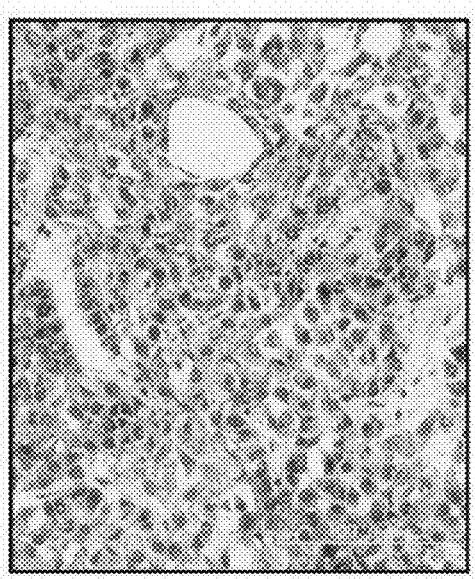
Figure 4:
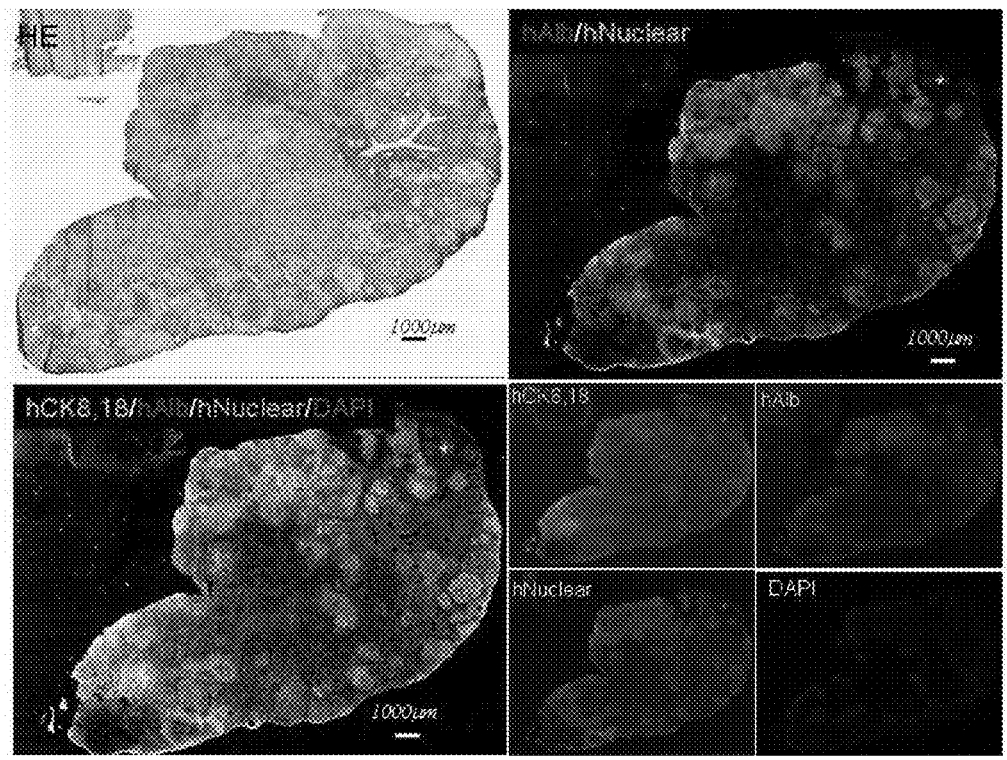
FIG. 4 shows the histological analysis of a humanized liver in a chimeric mouse (H & E staining and immunostaining). For more extensive histological analysis, chimeric liver tissues were H & E-stained and immunostained and then scanned by "Scan large imaging". The H & E staining showed widely engrafted human-derived hepatocytes and a large number of human cell-derived colonies (upper left image). The immunostaining showed that human nucleus-positive cells occupied approximately 50.0% of all stained cells in the liver (lower left image). In addition, human albumin-positive and human nucleus-positive cells were found, demonstrating that the transplanted human-derived hepatic stem cells are functional in the Alb-TRECK/SCID mouse liver (upper right image).

Histological Analysis of Humanized Liver in Chimeric Mouse (H & E Staining and Immunostaining) (FIGS. 3 and 4)

The produced human-derived chimeric liver was analyzed histologically. As a result of H & E staining, human-derived hepatic stem cells were observed (surrounded by dotted lines in FIG. 3).

For more extensive histological analysis, chimeric liver tissues were H & E-stained and immunostained and then scanned by "Scan large imaging". The H & E staining showed widely engrafted human-derived hepatocytes and a large number of human cell-derived colonies (upper left image of FIG. 4). The immunostaining showed that human nucleus-positive cells occupied approximately 50.0% of all stained cells in the liver (lower left image of FIG. 4). In addition, human albumin-positive and human nucleus-positive cells were found, demonstrating that the transplanted human-derived hepatic stem cells are functional in the Alb-TRECK/SCID mouse liver (upper right image of FIG. 4).

Figure 5:
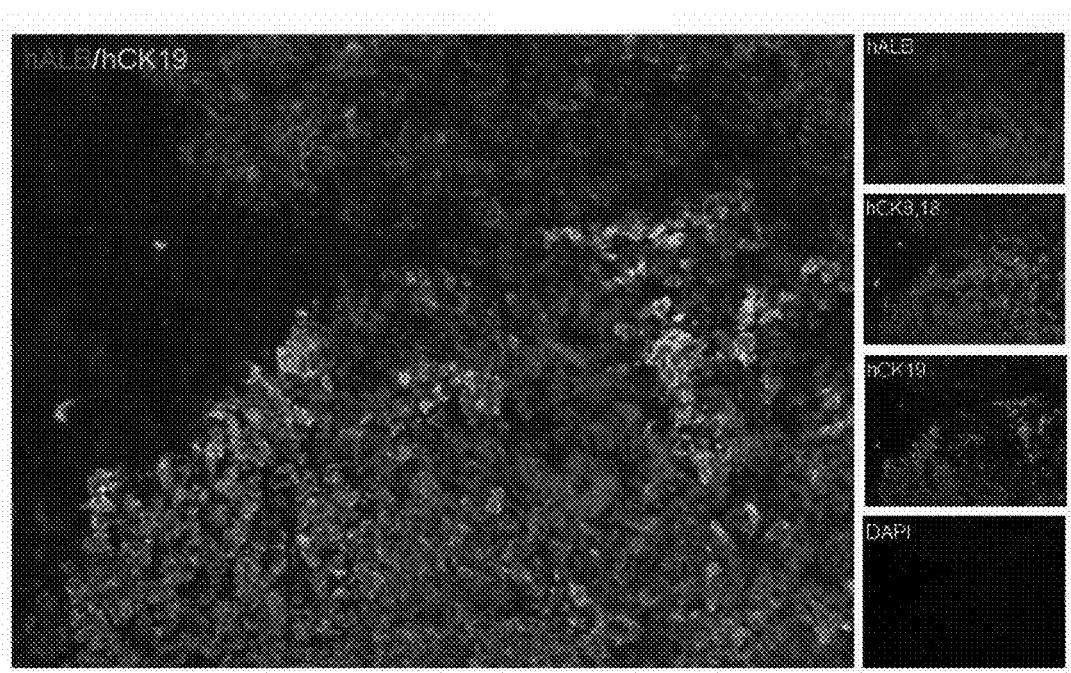
FIG. 5 shows the differentiation of human hepatic stem cells into hepatocytes in the mouse liver. Human albumin and human CK19 were immunostained in order to test whether transplanted human hepatic stem cells were induced to differentiate in an in vivo environment. A human albumin-positive/CK19-negative cell group was shown to have relatively high albumin secretion and express albumin at a level comparable to that of adult hepatocytes.
Figure 6:
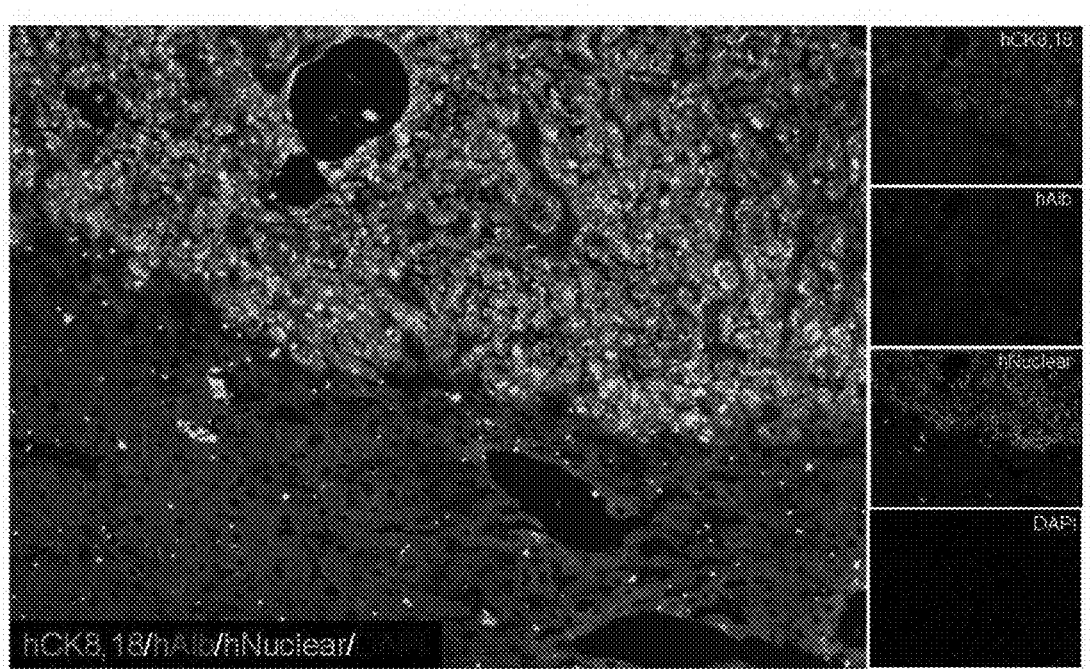
FIG. 6 shows the differentiation of human hepatic stem cells into hepatocytes in the mouse liver. Human albumin, human nuclear antigen, and human CK8/18 were immunostained in order to test whether transplanted human hepatic stem cells were induced to differentiate in an in vivo environment. The results of this immunostaining showed that human-derived cells were also present in large amounts in the mouse liver. The results shown in FIGS. 5 and 6 suggested that the transplanted hepatic stem cells are differentiated into two types of cells, hepatocytes and bile duct cells, in the recipient mouse liver and are capable of reconstituting tissues.

Differentiation of Human Hepatic Stem Cell into Hepatocyte in Mouse Liver (FIGS. 5 and 6)

Human albumin and human CK19 were immunostained in order to test whether transplanted human hepatic stem cells were induced to differentiate in an in vivo environment. A human albumin-positive/CK19-negative cell group was shown to have relatively high albumin secretion and express albumin at a level comparable to that of adult hepatocytes (FIG. 5). The results of immunostaining of human nuclear antigen and human CK8/18 showed that human-derived cells were also present in large amounts in the mouse liver (FIG. 6). These results suggested that the transplanted hepatic stem cells differentiate into two types of cells, hepatocytes and bile duct cells, in the recipient mouse liver and are capable of reconstituting tissues.

Figure 7:
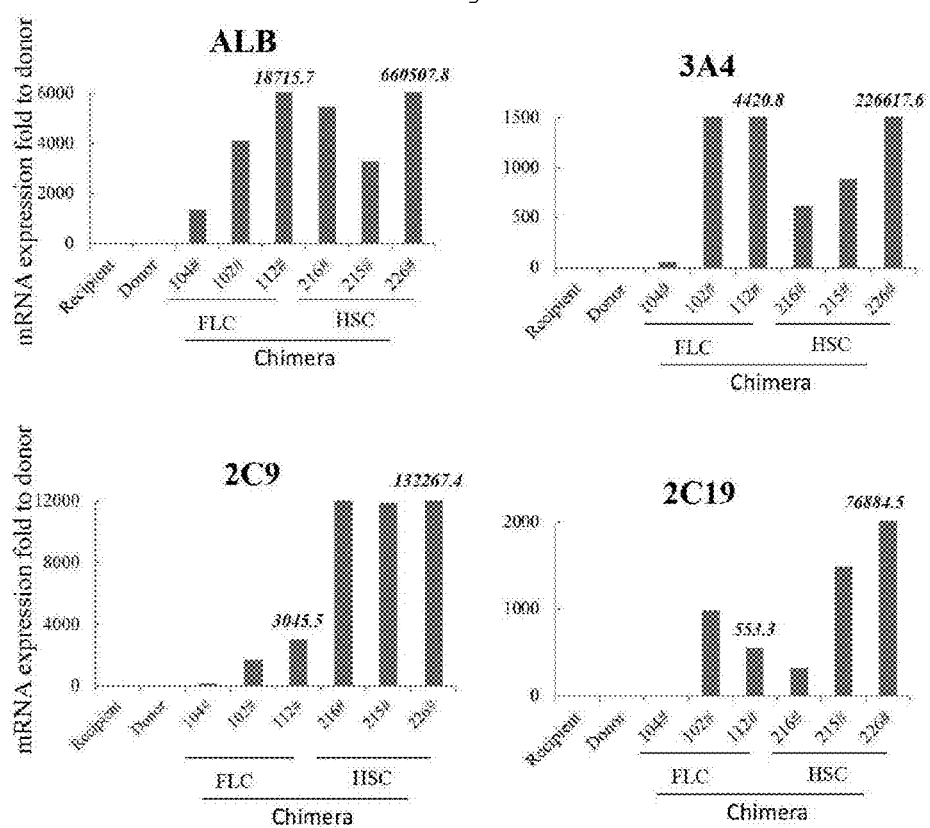
FIG. 7 shows the gene analysis of a humanized liver in a chimeric mouse. The in vivo analyses suggested the possibility that the human-derived chimeric liver would be functional. Thus, this chimeric liver was analyzed for gene expression. The expression of drug-metabolizing enzymes CYP3A4, CYP2C9, and CYP2C19, and hALB capable of liver-specific expression was analyzed by quantitative PCR. As a result, all the genes were expressed at increased levels in hepatic stem cell (HSC)-transplanted liver tissues, as compared with donor cells before transplantation. The rise in hALB gene expression was approximately 600000-fold and the rise in CYP3A4 expression was as high as approximately 227000-fold, suggesting that the hepatic stem cells were induced to differentiate in an in vivo environment. The hepatic stem cells were considered suitable for transplantation, because they showed higher gene expression and permitted easier induction of differentiation in the recipient liver than fetal liver cells. FLC: primary fetal liver cell; and HSC: hepatic stem cell.
Figure 8:
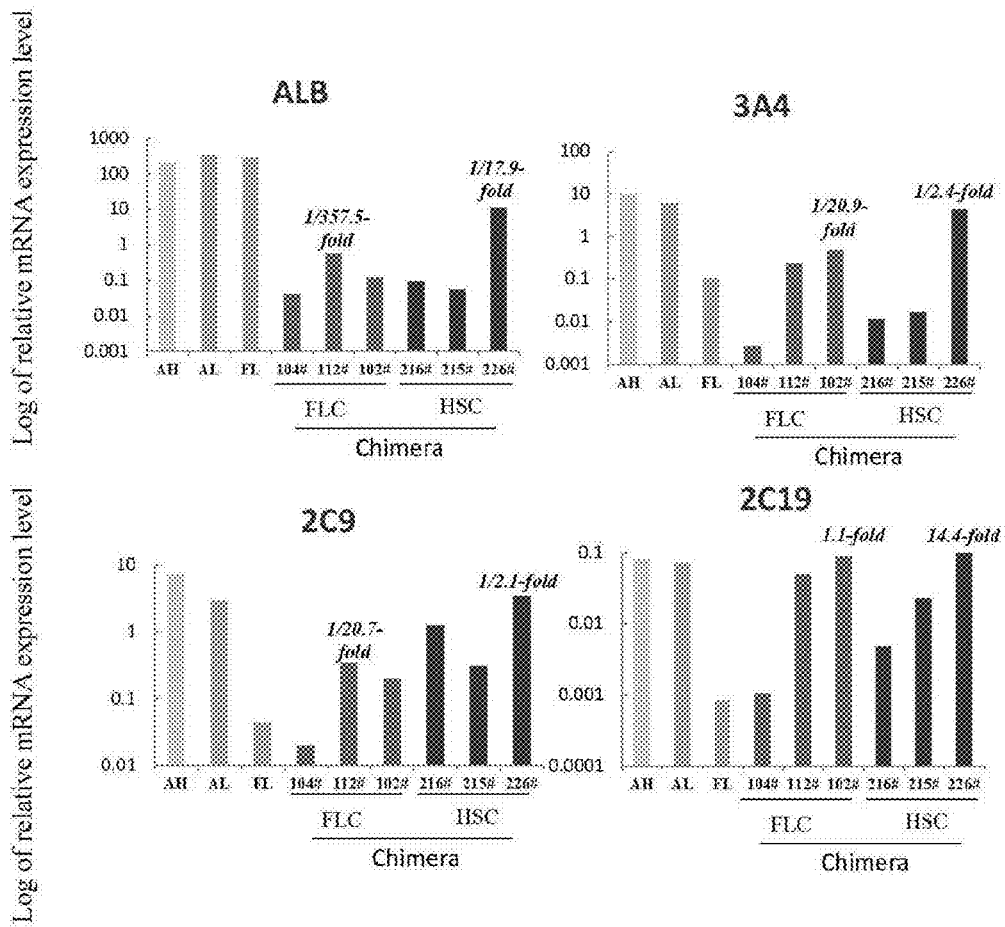
FIG. 8 The present inventors further compared gene expression among a humanized liver in a chimeric mouse (indicated by Chimera), adult hepatocytes (indicated by AH), adult liver tissues (indicated by AL), and fetal liver tissues (indicated by FL). Hepatic stem cell-derived chimeric liver tissues were found to express genes of CYPs at comparable levels to adult hepatocytes except for hALB gene expression (1/18) and, in particular, the expression of CYP2C19 was 10 times higher than that of AH.

Gene Analysis of Humanized Liver in Chimeric Mouse (FIGS. 7 and 8)

The in vivo analyses suggested the possibility that the human-derived chimeric liver would be functional. Thus, this chimeric liver was analyzed for gene expression. The expression of drug-metabolizing enzymes CYP3A4, CYP2C9, and CYP2C19, and hALB capable of liver-specific expression was analyzed by quantitative PCR. As a result, all the genes were expressed at increased levels in hepatic stem cell (HSC)-transplanted liver tissues, as compared with donor cells before transplantation (FIG. 7). The rise in hALB gene expression was approximately 660000-fold and the rise in CYP3A4 expression was as high as approximately 227000-fold, suggesting that the hepatic stem cells were induced to differentiate in an in vivo environment. The hepatic stem cells were considered suitable for transplantation, because they showed higher gene expression and permitted easier induction of differentiation in the recipient liver than fetal liver cells.

The present inventors further compared gene expression among a humanized liver in a chimeric mouse (indicated by Chimera), adult hepatocytes (indicated by AH), adult liver tissues (indicated by AL), and fetal liver tissues (indicated by FL). Hepatic stem cell-derived chimeric liver tissues were found to express genes of CYPs at comparable levels to adult hepatocytes except for hALB gene expression (1/18) and, in particular, the expression of CYP2C19 was 10 times higher than that of AH (FIG. 8).

Figure 9:
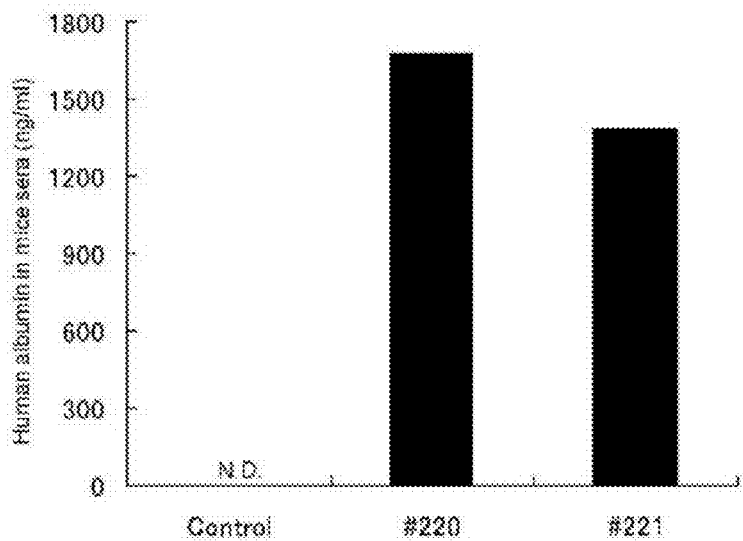
FIG. 9 shows the albumin secretion assay of a human-derived chimeric liver. The preceding analyses suggest that the hepatic stem cell-derived chimeric liver is functional. Thus, the present inventors analyzed the amount of human albumin secreted into chimeric mouse serum by ELISA. Human albumin was not detected in the serum of a non-transplant Alb-TRECK/SCID mouse used as a control (indicated by Control). By contrast, mice (#220 and #221) having a human-derived chimeric liver resulting from the transplantation of hepatic stem cells were confirmed to have human albumin secreted in 1679 ng/ml and 1381 ng/ml, respectively, into the serum 50 days after the transplantation. These results demonstrated that the transplanted hepatic stem cells differentiate into functional cells in the Alb-TRECK/SCID mouse liver.

Albumin Secretion Assay of Human-Derived Chimeric Liver (FIG. 9)

The preceding analyses suggest that the hepatic stem cell-derived chimeric liver is functional. Thus, the present inventors analyzed the amount of human albumin secreted into chimeric mouse serum by ELISA. Human albumin was not detected in the serum of a non-transplant TRECK/SCID mouse used as a control (indicated by Control). By contrast, mice (#220 and #221) having a human-derived chimeric liver resulting from the transplantation of hepatic stem cells were confirmed to have human albumin secreted in 1679 ng/ml and 1381 ng/ml, respectively, into the serum 50 days after the transplantation. These results demonstrated that the transplanted hepatic stem cells differentiate into functional cells in the TRECK/SCID mouse liver. Chimeric mice having a humanized liver resulting from the transplantation of hepatic stem cells and primary fetal liver cells were also observed to have a survival time exceeding 120 days.

Figure 10:
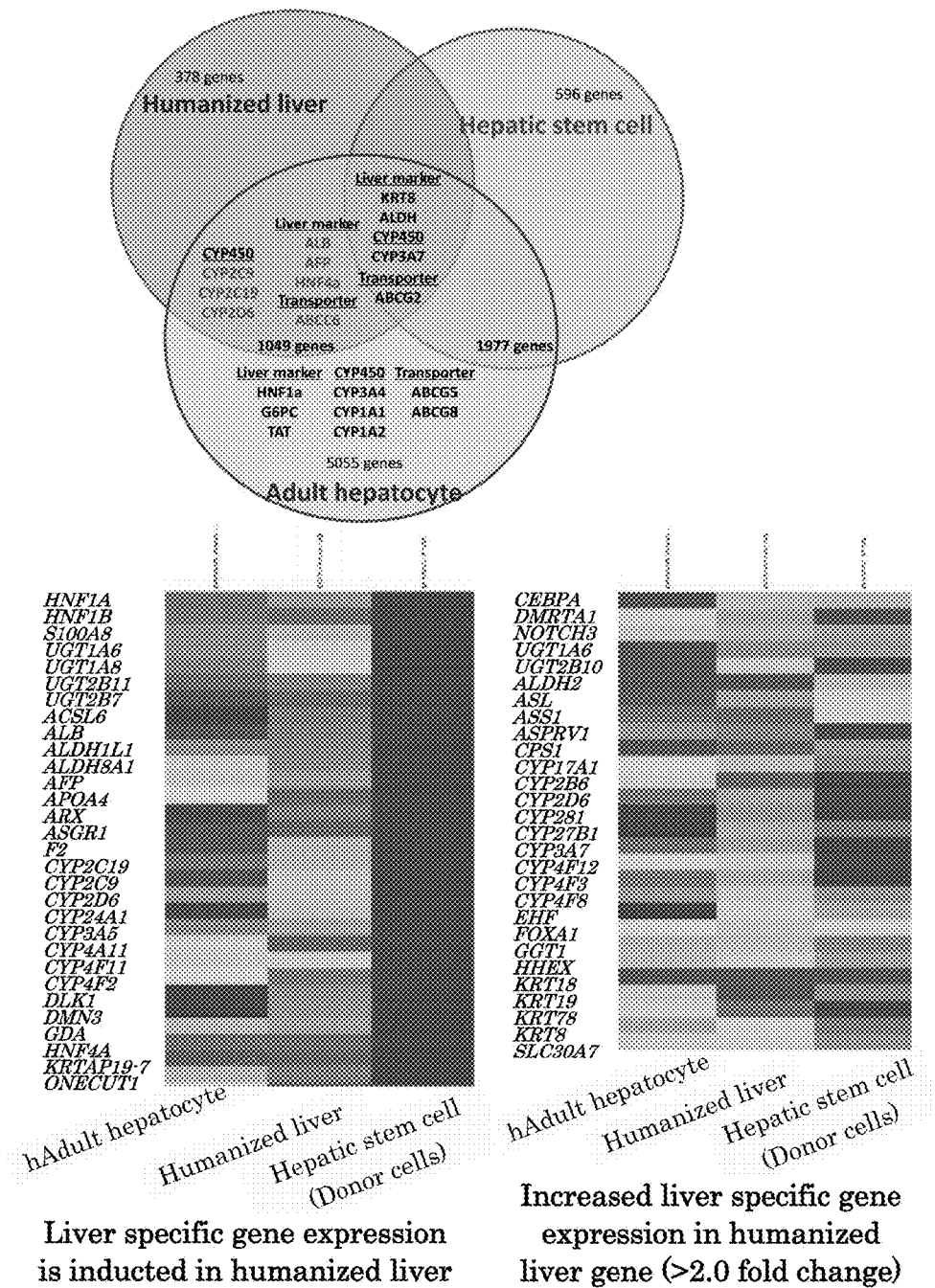
FIG. 10 shows the microarray analysis of a humanized liver.

Microarray Analysis of Humanized Liver (FIG. 10)

Comprehensive gene expression profiles were analyzed in order to test the degree of cell differentiation in a human fetal hepatic stem cell-derived chimeric liver generated in a mouse liver. Fetal hepatic stem cells (donor cells) and human adult hepatocytes (XenoTech Cat No: H1500.H15A+) were used as groups to be tested and compared for expression patterns. As a result, the expression of 1049 genes was confirmed only in the chimeric liver and the adult hepatocytes and not in the fetal hepatic stem cells. Among these gene products, ALB, AFP, and HNF4a used as liver-specific markers, as well as drug-metabolizing enzymes CYP2C9, CYP2C19, and CYP2D6 were confirmed. While the microarray contained a total of 53 CYP gene probes, 27 genes were detectably expressed in the chimeric liver. Since 49 genes were expressed in the adult hepatocytes and 15 genes in the fetal hepatic stem cells, it is suggested that in the chimeric liver, induction for differentiation proceeded to cause differentiation into adult hepatocytes. In addition, there was confirmed the expression of functional genes involved in lipid metabolism, ammonia metabolism, or alcohol metabolism. As a result of testing genes that were expressed in the chimeric liver at least twice the level of expression in the fetal hepatic stem cells, various CYP genes, genes of liver markers CEBPA and KRT, and genes involved in various kinds of metabolism were found to increase in the level of expression. This suggested that in the in vivo environment in the mouse, the human fetal hepatic stem cells undergo promoted induction for differentiation and reconstitute liver tissues as they gradually differentiate into adult hepatocytes.

The donor cells used were CDCP1-positive/CD90-positive/CD66-negative cells as separated by FACS from human primary fetal hepatocytes supplied by Dainippon Pharmaceutical Co., Ltd. (Cat No. CS-ABI-3716) or cultured or subcultured cells thereof. Preparation methods for these cells are described in WO2009/139419.

Figure 11:
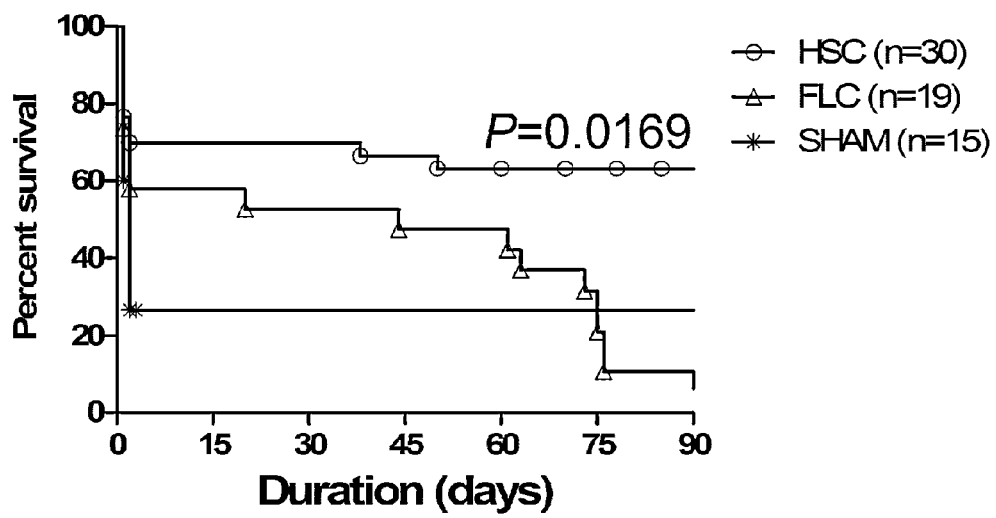
FIG. 11 shows the survival rate of a chimeric mouse.

Survival Rate of Chimeric Mouse (FIG. 11)

The produced chimeric mice having human hepatocytes were analyzed for survival rate in order to examine whether or not their livers were functional to have therapeutic effects on liver damage. As a result, the transplant group had a significantly higher survival rate than a non-transplant control (SHAM) group, suggesting that the human fetal liver cells are functional in the mouse liver. The human hepatic stem cell-transplanted mice were able to survive for a significantly long duration, compared with the control group (SHAM) (P=0.0169, Log-rank (Mantel-Cox) test). These mice are also applicable as systems for in vivo evaluation of toxicity against or drug efficacy for human hepatocytes.

Capacity to Metabolize Drugs (for Confirmation of Human-Specific Metabolites in a Humanized Chimeric Mouse (FIG. 12))

Ketoprofen was intravenously administered at a dose of 15 mg/kg to human hepatocyte-transplanted TRECK/SCID mice. Sham-operated mice were used as a control. Urine (0-4 hrs) was collected into 0.5 M acetate buffer (pH 5.0). 1 N KOH was added to the urine samples, which were then incubated at 80° C. for 3 hours and thereafter neutralized by use of an equal volume of 1 N HCl. Acetonitrile containing 1% acetic acid was added and the mixture was centrifuged (15000 rpm, 4° C., 5 min). The supernatant was subjected to liquid chromatography-tandem mass spectrometry (LC/MS/MS). An LC-20A series (Shimadzu, Kyoto, Japan) equipped with an Inertsil ODS-3 column (GL Sciences Inc., Tokyo, Japan) was used for the liquid chromatography experiment. Chromatographic separation was achieved on Inertsil ODS-3 column (5 µm, 4.6×150 mm I.D.; GL Sciences Inc., Tokyo, Japan). The temperature of the column was kept at 40° C. A mobile phase consisting of 0.1% acetic acid (solvent A) and acetonitrile containing 0.1% acetic acid (solvent B) was pumped in at a flow rate of 0.5 mL/min according to the following gradient schedule: a linear gradient from 25 to 80% solvent B (0-15 min), 80% solvent B (15-25 min), a linear gradient from 80 to 25% solvent B (25-26 min), and 25% solvent B (26-35 min). The liquid chromatography apparatus was connected to a 4000 Q Trap system (AB SCIEX, Foster City, Calif.) and operated in negative electrospray ionization mode. The turbo gas was kept at 600° C. Parent and/or fragment ions were filtered in the first quadrupole and dissociated in the collision cell using nitrogen as collision gas. The ion spray voltage was set to a value of −4500 V. The analysed m/z transitions (Q1/Q3) for ketoprofen and 1-hydroxyketoprofen were 253.1/209.3 and 269.1/209.3, respectively.

KTP is primarily metabolised by cytochrome P450 in mice to form 1-hydroxyketoprofen (OH-KTP). On the other hand, in humans, KTP is mainly metabolised by UDP-glucuronosyltransferase (UGT) to form ketoprofen glucuronide (KTP-G).

Liver-humanised mice serve as a useful tool for studying human-specific drug metabolisms. Human-specific drug metabolism functions in liver-humanised mice have been previously reported using high-quality adult hepatocytes and immunodeficient mice having a severely damaged liver. The administered KTP was observed to be easily glucuronidated by the action of UGT and metabolised to KTP-G through hydrolysis. The KTP/OH-KTP peak area ratio was calculated and compared between hydrolysis and non-hydrolysis samples. The fold increase of the KTP/OH-KTP peak area ratio suggests the formation of KTP-G in samples. The fold increases in the urines of the human hepatocyte-transplanted TRECK/SCID mice (n=8) and the control mice (n=3) suggest that KTP glucuronidation (human-specific drug metabolism function) is observed in the human hepatocyte-transplanted TRECK/SCID mice.

Debrisoquine, which serves as a common phenotyping agent for human CYP2D6, is metabolized to 4-hydroxydebrisoquine (4-OHDB) in humans but is negligible in mice. Importantly, human CYP2D6 is involved in the metabolism of 25% of known drugs and contributes to pronounced inter-individual variability because it occurs in a large number of polymorphisms. The plasma concentration of 4-OHDB following the oral administration of debrisoquine was higher in the chimera group than in the sham-operated group, reflecting the production of human-specific drug metabolites.

Figure 12:
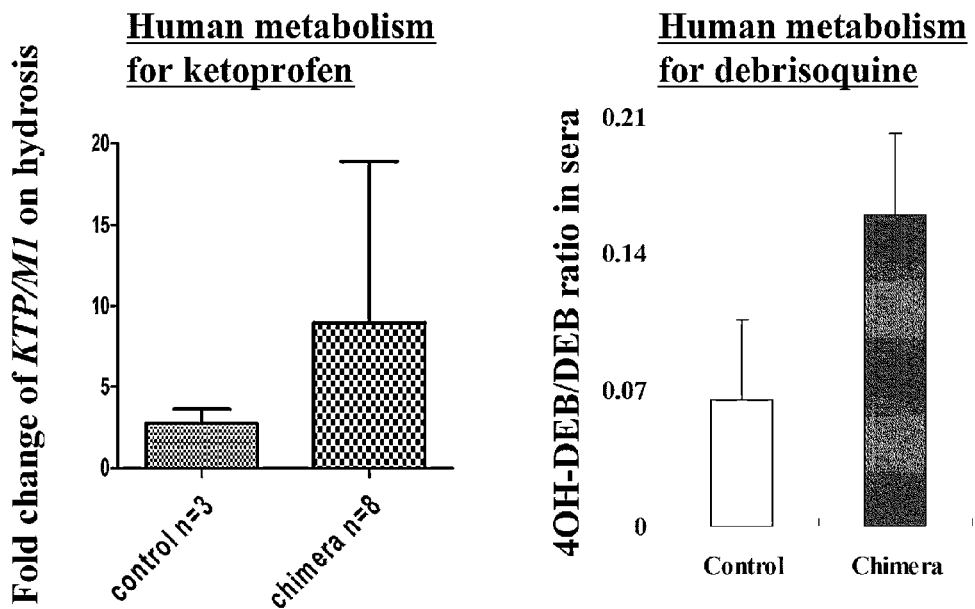
FIG. 12 shows the capacity to metabolize drugs (for confirmation of human-specific metabolites in a humanized chimeric mouse).

The right diagram of FIG. 12 shows the serum ratio of debrisoquine metabolite 4-OHDB to debrisoquine in the chimeric mice (n=3) and the control mice (n=4). Debrisoquine was orally administered at a dose of 2.0 mg/kg. The data was obtained 8 hours after the oral administration and is indicated by the mean±SD.

Figure 13:
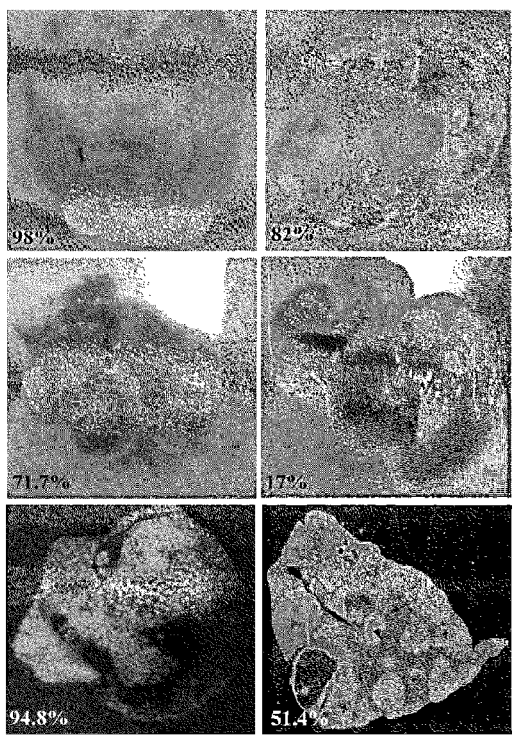
FIG. 13 shows the chimera rate of a humanized liver in a chimeric mouse.
Figure 13:
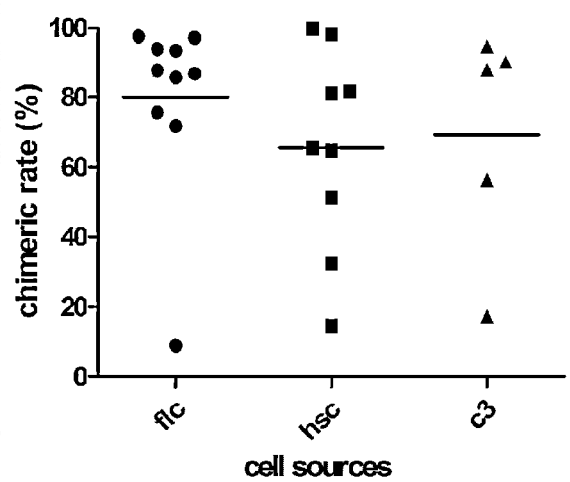

Chimera Rate of Humanized Liver in Chimeric Mouse (FIG. 13)

Human fetal liver cells, hepatic stem cells, or stem cells of a line with self-renewal capacity enhanced by BMI introduction (see WO2009/139419) were transplanted to liver damaged TRECK/Scid mice. Reconstituted mouse livers were sampled 40 days after the transplantation and analyzed histologically. Sampling and histological analysis were performed approximately 3 to 7 weeks after the transplantation. Quantitative PCR was performed in order to conduct more detailed study on chimera rate. Primers were designed and prepared as sequences for detection of a mouse ACTB-specific sequence, a human ACTB-specific sequence, and ACTBs of both species. As a result of determining the chimera rate, the following high average chimera rates were obtained: FLC, 79.9±26.4% (mean±SD, n=10); HSC, 65.5±28.9% (n=9); and BMI1 clone 3, 69.3±32.9% (n=5). In individuals having the highest chimera rate, mouse hepatocytes were replaced with HSCs in high efficiency at 99.9% and 98.4%.

Primers for Detection of Human ACTS-Specific Sequence:

```
                                           (SEQ ID NO: 1)
       hACTB F gcacaatgaagatcaagatcattg (SEQ ID NO: 2)
       hACTB R taaagccatgccaatctcatc
```

Primers for Detection of Mouse ACTB-Specific Sequence:

```
                                           (SEQ ID NO: 3)
       mACTB F aagatcaagatcattgctcctcct (SEQ ID NO: 4)
       mACTB R gccatgccaatgttgtctctta
```

Primers for Detection of ACTBs of Both Human and Mouse Species:

```
                                           (SEQ ID NO: 5)
       hm ACTB F gcaccacaccttctacaatga (SEQ ID NO: 6)
       hm ACTB R gctggggtgttgaaggtctc
```

Example 2

Production of Chimeric Mouse Using uPA-NOG uPA-NOG (uPA-NOD/scid Il2KO) immunodeficient mice with spontaneous liver damage which would express mouse urokinase-type plasminogen activator (uPA) in a liver-specific manner using mouse albumin gene enhancer/promoter were provided by the Central Institute for Experimental Animals.

Figure 14:
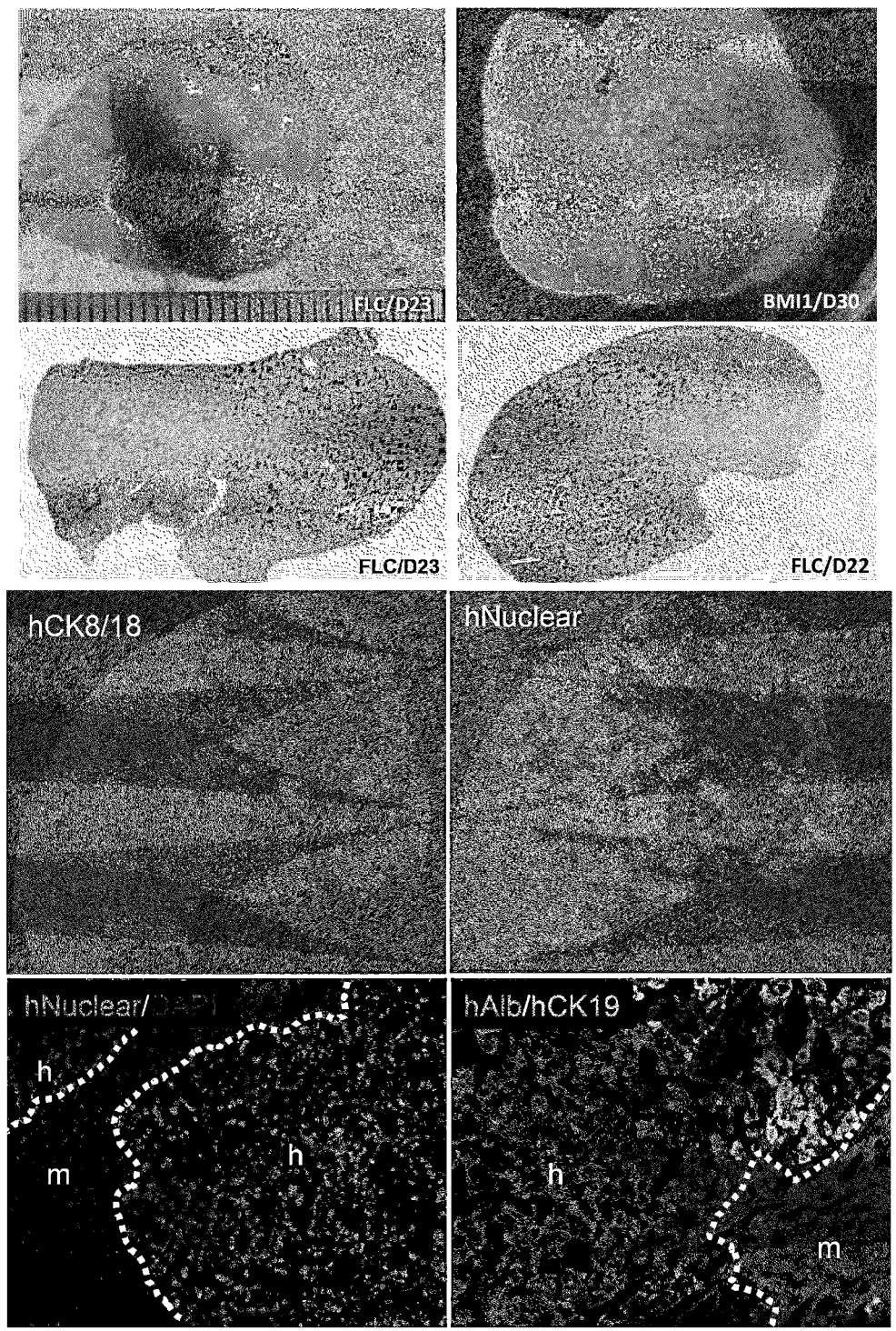
FIG. 14 shows the histological analysis of a humanized liver in a chimeric mouse (H & E staining and immunostaining).

Histological Analysis of Humanized Liver in Chimeric Mouse (H & E Staining and Immunostaining) (FIG. 14)

GFP-expressing hepatic stem cells were used in transplantation in order to visualize the engrafted state, of transplanted hepatic stem cells more precisely. Thirty days after the transplantation, almost 100% of cells in the liver tissues were derived from GFP-positive hepatic stem cells. For more extensive histological analysis, chimeric liver tissues were H & E-stained and immunostained and then scanned by "Scan large imaging". The H & E staining showed widely engrafted human-derived hepatocytes and a large number of human cell-derived colonies. The immunostaining showed that human nucleus-positive cells occupied at least about 50.0% of all stained cells in the liver. In addition, human albumin-positive and human nucleus-positive cells were found, demonstrating that the transplanted human-derived hepatic stem cells are functional in the uPA-NOG mouse liver. Cells coexpressing a liver parenchymal cell marker ALB and a bile duct epithelial cell marker CK19 were found, suggesting that some cells differentiated into two types of cells, hepatocytes and bile duct epithelial cells.

Figure 15:
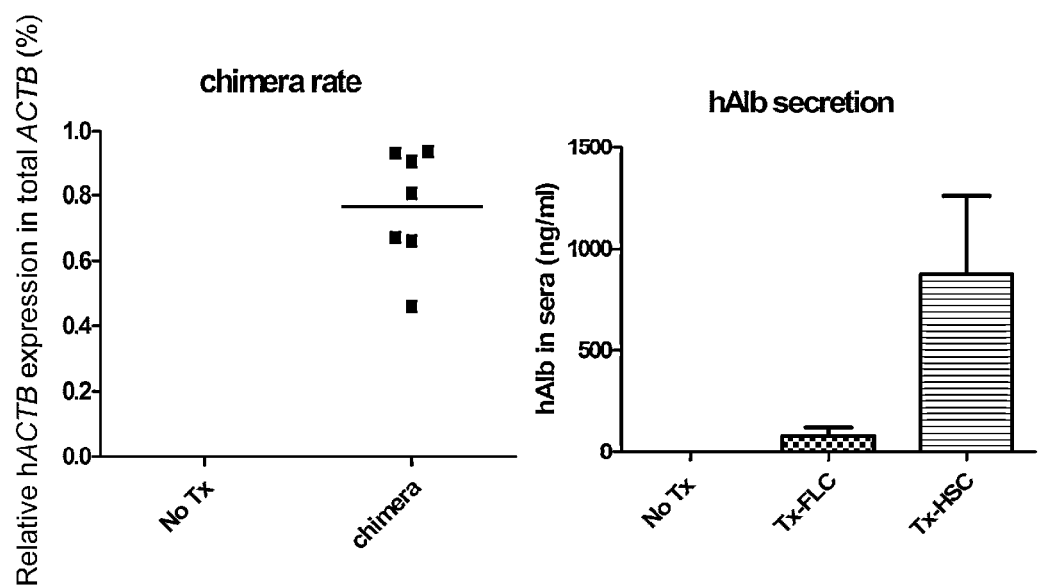
FIG. 15 shows the chimera rate of a humanized liver in a chimeric mouse and the secretion of human albumin.

Chimera Rate of Humanized Liver in Chimeric Mouse and Secretion of Human Albumin (FIG. 15)

Immature human hepatocytes were transplanted to uPA-NOG mice with spontaneous liver damage to reconstitute mouse livers. Liver tissues and serum were sampled 4 to 7 weeks after the transplantation and examined by quantitative PCR to investigate the chimera rate. Primers were designed and prepared as sequences for detection of a mouse ACTS-specific sequence, a human ACTB-specific sequence, and ACTBs of both species. As a result of determining the chimera rate, the following high average chimera rate was obtained: 76.6±17.7% (mean±SD, n=10). In an individual having the highest chimera rate, mouse hepatocytes were replaced with HSCs in high efficiency of 93.3%. The mouse serum was further examined by ELISA for the presence of human albumin. No human albumin was detected in non-transplant mice, whereas the secretion of 1000 ng/ml serum albumin and human albumin was confirmed in the human hepatic stem cell-derived transplant group.

Figure 16:
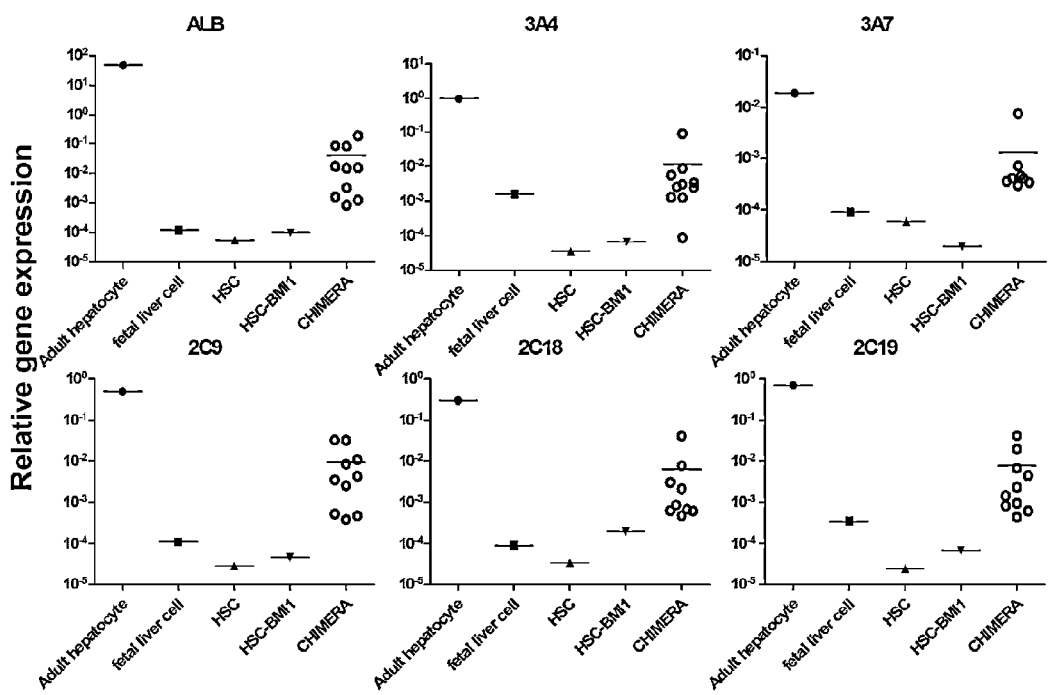
FIG. 16 shows the gene analysis of a humanized liver in a chimeric mouse.

Gene Analysis of Humanized Liver in Chimeric Mouse (FIG. 16)

The in vivo analyses suggested the possibility that the human-derived chimeric liver would be functional. Thus, this chimeric liver was analyzed for gene expression. The expression of drug-metabolizing enzymes CYP2C9, CYP2C18, CYP2C19, CYP3A4, and CYP3A7, and hALB capable of liver-specific expression was analyzed by quantitative PCR. As a result, all the genes were expressed at increased levels in the recipient liver tissues, compared with the donor cells before transplantation. Some samples were found to express genes of CYPs at comparable levels to adult hepatocytes, suggesting that the immature hepatocytes were induced to differentiate in the in vivo environment.

All publications, patents, and patent applications cited herein are incorporated herein by reference in their entirety.

INDUSTRIAL APPLICABILITY

According to the present invention, adult hepatocytes can be obtained by inducing separated hepatic stem/progenitor cells or immature human hepatocytes to differentiate in vivo in a non-human animal. The resulting products can make a great contribution to artificial livers, in vitro drug metabolism tests, etc. Also, a human hepatocyte-chimerized non-human animal can be obtained. Use of this chimeric non-human animal will enable the performance of drug metabolism tests or stability tests on candidate compounds in drug discovery.

The chimeric non-human animal having a human liver, as obtained according to the present invention, can be used as a laboratory animal in research for drug discovery, including drug metabolism tests, stability tests, and screening for drug efficacy. In addition, adult hepatocytes obtained by induction for differentiation in vivo are useful for in vitro research for drug discovery or as a source for artificial livers.

Free Text for Sequence Listing
<SEQ ID NO: 1>
SEQ ID NO: 1 represents the nucleotide sequence of a forward primer for detection of a human ACTB-specific sequence.
<SEQ ID NO: 2>
SEQ ID NO: 2 represents the nucleotide sequence of a reverse primer for detection of a human ACTB-specific sequence.
<SEQ ID NO: 3>
SEQ ID NO: 3 represents the nucleotide sequence of a forward primer for detection of a mouse ACTB-specific sequence.
<SEQ ID NO: 4>
SEQ ID NO: 4 represents the nucleotide sequence of a reverse primer for detection of a mouse ACTB-specific sequence.

<SEQ ID NO: 5>
SEQ ID NO: 5 represents the nucleotide sequence of a forward primer for detection of ACTBs of both human and mouse species.

<SEQ ID NO: 6>
SEQ ID NO: 6 represents the nucleotide sequence of a reverse primer for detection of ACTBs of both human and mouse species.

The invention claimed is:

1. A method for producing an immunodeficient non-human animal having a humanized liver expressing a human-derived drug-metabolizing enzyme, comprising:
   transplanting human hepatic stem cells, human hepatic progenitor cells, and/or human immature hepatocytes to a liver-damaged immunodeficient non-human animal via spleen or portal vein to induce the differentiation of the cells into hepatocytes, wherein the human hepatic stem cells, human hepatic progenitor cells, and/or human immature hepatocytes are CDCP1-positive/CD90-positive/CD66-negative cells,
   wherein the non-human animal is selected from the group consisting of a TRECK mouse and an uPA-NOG mouse,
   wherein the TRECK mouse has a high chimera rate of human hepatocytes of up to 99.9%, and wherein the uPA-NOG mouse has a high chimera rate of human hepatocytes of up to 93.3%, and
   wherein the TRECK mouse has a survival time exceeding 120 days.

2. The method according to claim 1, wherein the liver damage is hepatocyte-specific.

3. The method according to claim 1 or 2, wherein the immunodeficient TRECK mouse with hepatitis is caused by the administration of diphtheria toxin to an immunodeficient TRECK mouse that expresses a diphtheria toxin receptor human HB-EGF in hepatocytes.

4. The method according to claim 1, wherein the uPA-NOG immunodeficient mouse with spontaneous liver damage expresses urokinase-type plasminogen activator in a liver-specific manner using albumin gene enhancer/promoter.

5. The method according to claim 1, wherein the human hepatic stem cells and/or hepatic progenitor cells and/or immature hepatocytes are CDCP1-positive/CD90-positive/CD66-negative/CD13-positive cells.

6. A TRECK mouse or an uPA-NOG mouse having a humanized liver, produced by a method according to claim 1.

7. A method for examining the pharmacokinetics of a test substance, comprising:
   administering the test substance to the TRECK mouse or uPA-NOG mouse having a humanized liver according to claim 6; and
   assaying metabolites, excrement, plasma or liver tissue recovered from the TRECK mouse or uPA-NOG mouse having a humanized liver to determine the pharmacokinetics of the test substance.

8. A method for examining the hepatotoxicity of a test substance, comprising:
   (a) administering the test substance to the TRECK mouse or uPA-NOG mouse having a humanized liver according to claim 6; and
   (b1) assaying human albumin, transaminase (GOT), alanine transaminase (GPT) or lactate dehydrogenase (LDH) in a blood sample of the TRECK mouse or uPA-NOG mouse having a humanized liver to determine the hepatotoxicity of the test substance, or
   (b2) assaying whether hepatocytes from the TRECK mouse or uPA-NOG mouse having a humanized liver after administration of the test substance exhibit necrosis.

\* \* \* \* \*